United States Patent [19]

Barbera Alacreu

[11] Patent Number: 6,001,102
[45] Date of Patent: Dec. 14, 1999

[54] TRANSPEDICULAR VERTEBRAL ATTACHMENT SYSTEMS AND DEVICE FOR THE PRACTICE THEREOF

[75] Inventor: Jose Vicente Barbera Alacreu, Juan Martorell 1, bajo-46010-Valencia, Spain

[73] Assignees: Jose Vicente Barbera Alacreu; Jose J. Aparici Marin; Jose Ramon Bilbao Ortiz De Zarate, all of Valencia, Spain

[21] Appl. No.: 08/970,382

[22] Filed: Nov. 14, 1997

Related U.S. Application Data

[63] Continuation of application No. 08/355,258, Dec. 8, 1994, abandoned.

[51] Int. Cl.⁶ .................................................. A61F 5/04
[52] U.S. Cl. .................................................. 606/73
[58] Field of Search ........................... 606/61, 72, 73, 606/80, 96, 104; 623/17

[56] References Cited

U.S. PATENT DOCUMENTS 4,611,581  9/1986  Steffee ....................... 606/61
4,716,893  1/1988  Fischer et al. ............. 606/75 X
5,059,193  10/1991  Kuslich ....................... 606/61

FOREIGN PATENT DOCUMENTS 3509417  9/1986  Germany ..................... 606/73
584855  12/1977  Russian Federation ..... 606/73

*Primary Examiner*—Michael Buiz
*Assistant Examiner*—Vy Quang Bui
*Attorney, Agent, or Firm*—Birch, Stewart, Kolasch & Birch, LLP

[57] ABSTRACT

In transpedicular vertebral attachment systems and a device for the practice thereof a screw is provided. The screw is much shorter than a traditional screw and engages a plug of silastic or any other polymer having equivalent mechanical properties and biocompatibility, such as a metal or metal alloy. The plug is inserted in the pedicle, extending only slightly beyond the length thereof. The system is applicable to osteoporotic patients in whom the density of the bone tissue of the vertebral body is much lower, and in general in all lesions of the backbone in which instrumented vertebral fusion is indicated.

19 Claims, 3 Drawing Sheets

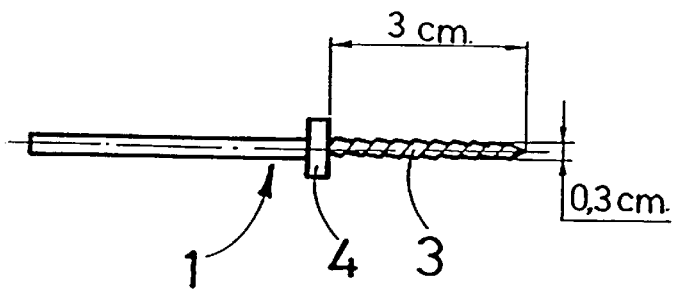
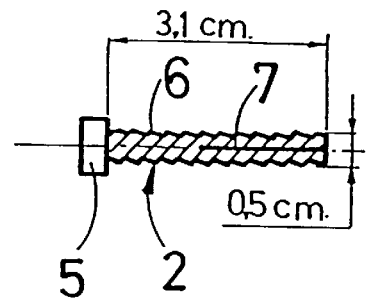
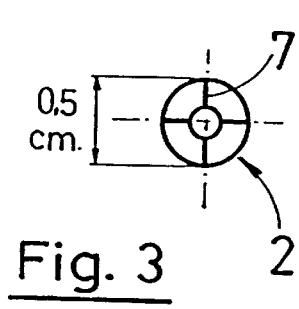
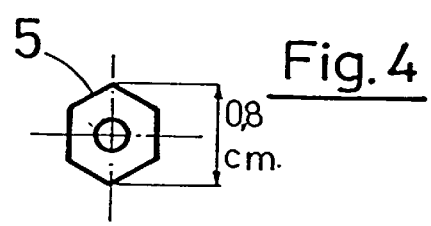
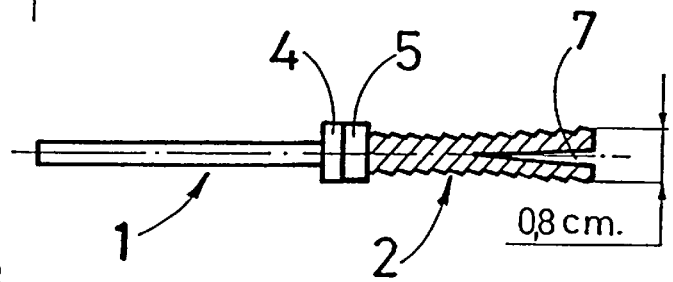
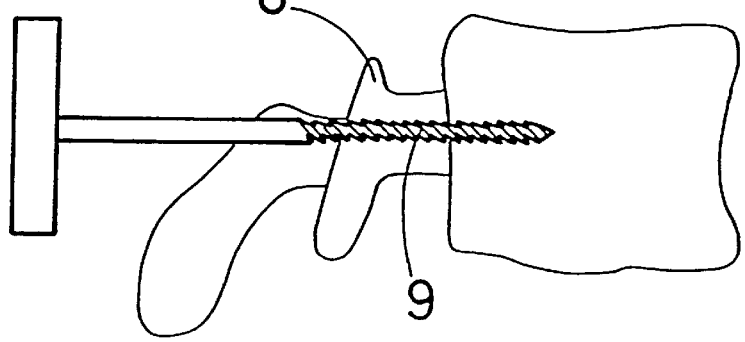
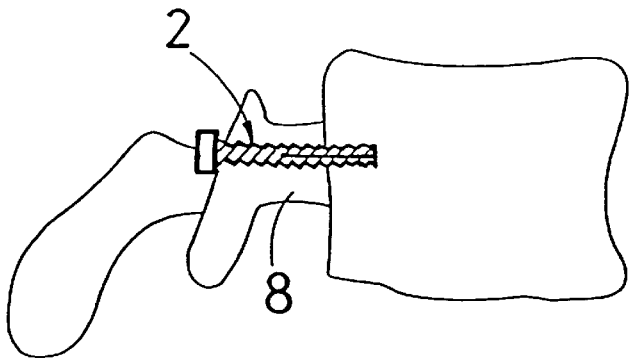

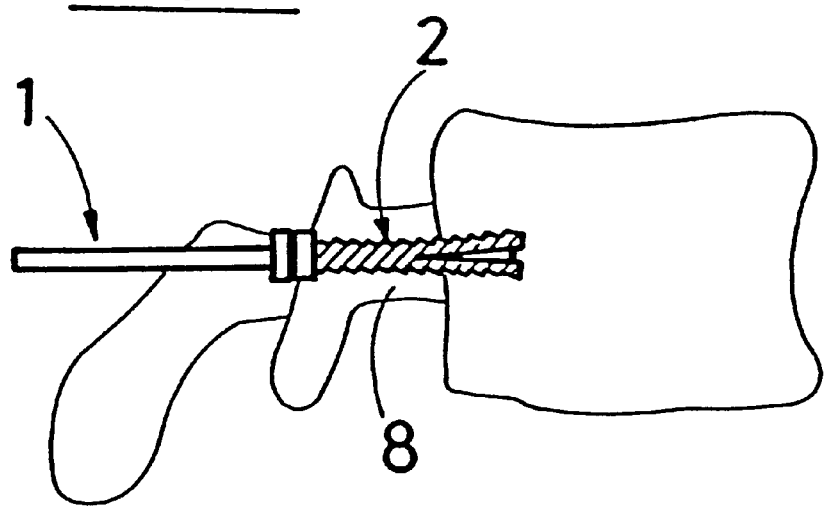
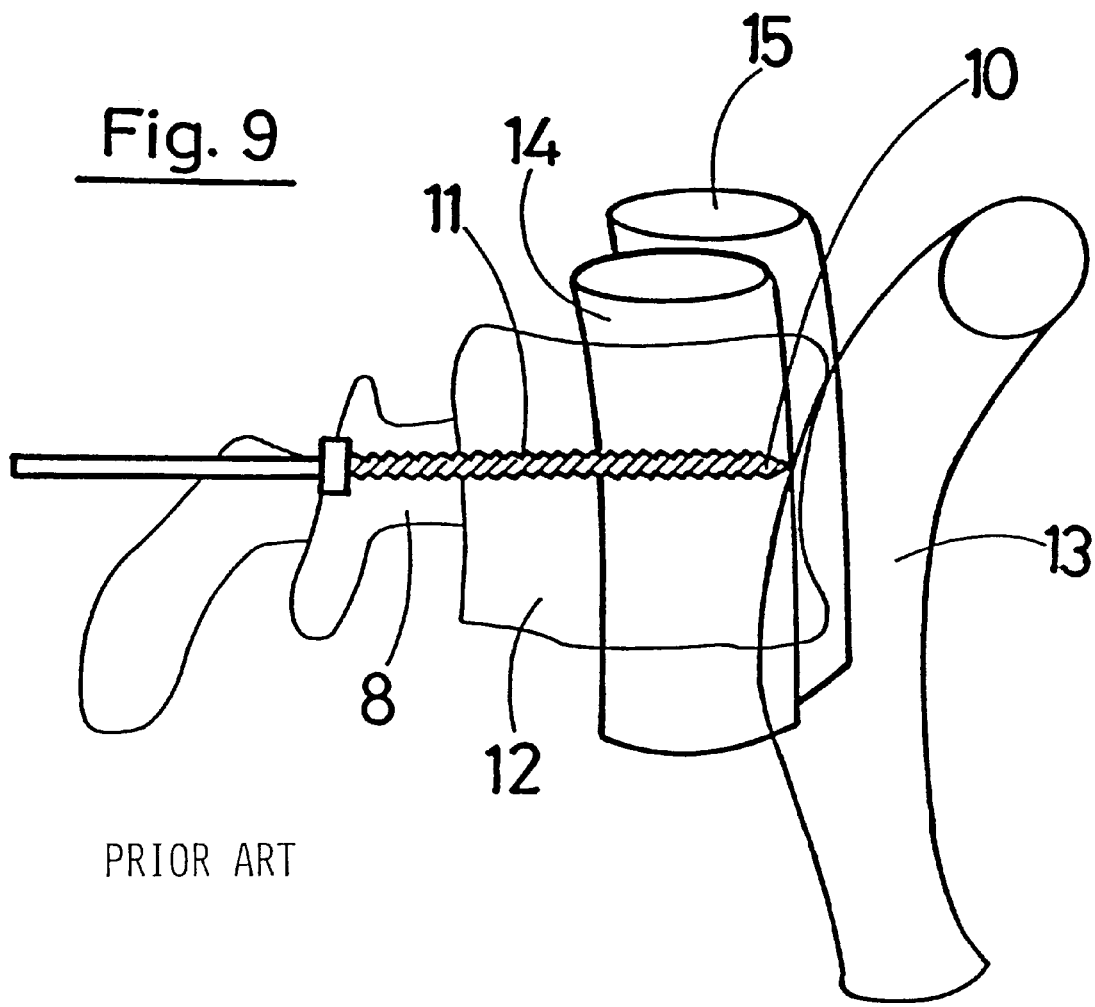
PRIOR ART

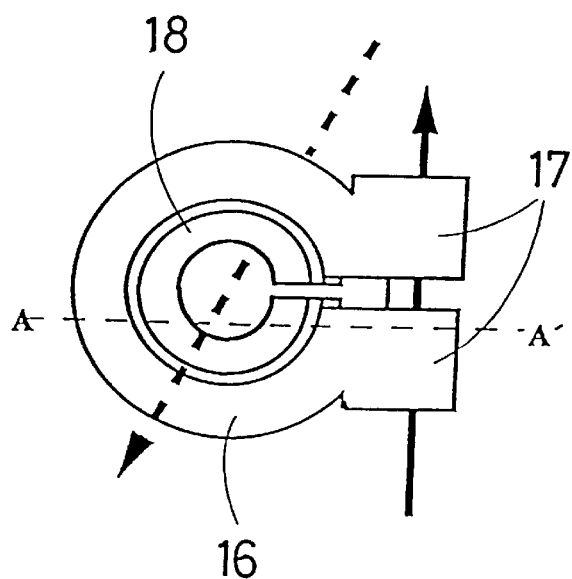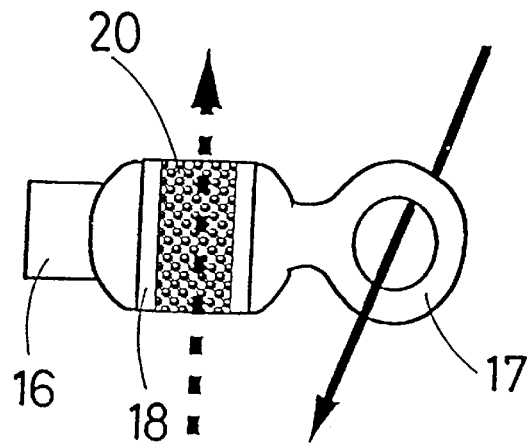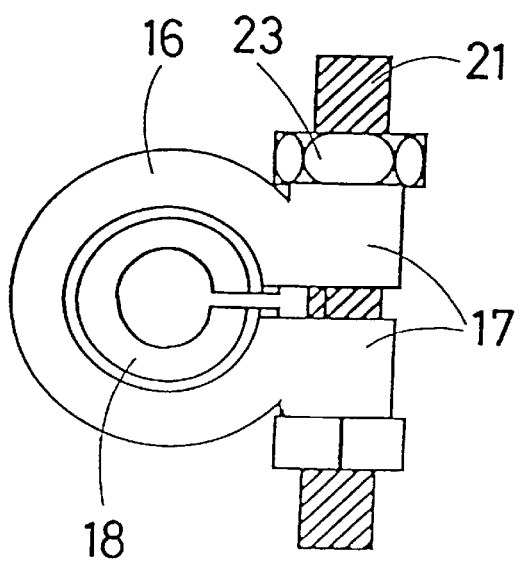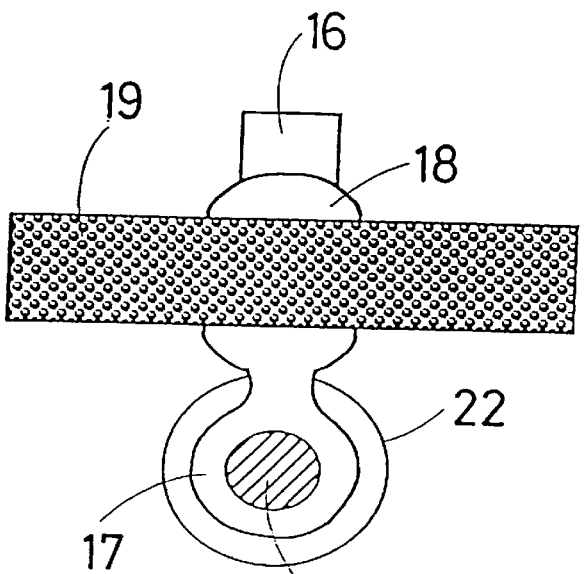

TRANSPEDICULAR VERTEBRAL ATTACHMENT SYSTEMS AND DEVICE FOR THE PRACTICE THEREOF

This application is a continuation of application Ser. No. 08/355,258 filed on Dec. 8, 1994, now abandoned.

FIELD OF THE INVENTION

This present invention relates to improvements in transpedicular vertebral attachment systems and a device for the practice thereof, providing for their intended function various advantages to be described hereinafter, apart from others inherent in the organization and constitution thereof.

BACKGROUND OF THE INVENTION

There is currently known the technique regularly used for transpedicular vertebral attachment using a normal five centimeter long screw.

This technique suffers from drawbacks derived from the very dimension and constitution of the screw and of the anchorage site, which may cause rocking of the front end of the screw, proper to osteoporotic vertebrae, with the consequent loss of pull-out strength and with the serious risk of extending beyond the vertebra anterior cortical layer with the tip of the screw, possibly perforating viscera or blood vessels.

SUMMARY OF THE INVENTION

The present inventor has devised improvements in transpedicular vertebral attachment systems of the type described above, comprising of replacing the traditional length screws with another much shorter screw applied on a plug of silastic or any other polymer of similar mechanical features and biocompatibility, or any metal or alloy, which is inserted in the pedicle and being only slightly longer than the latter.

The objective is that when the screw is screwed into the plug, the front inner end of the latter is widened on being expanded by the screw.

The following purposes are obtained:

1) a shorter screw, avoiding the danger of perforating viscera or blood vessels, which may happen when the conventional screws are used.

2) a greater resistance to pull-out forces, since the inner end of the plug is much wider than the outer end, preventing it from being forced out backwards. Likewise, since an exclusively pedicular anchorage is available, this being the strongest part of the vertebra, the possibility of rocking movements of the front end of the screw, proper to osteoporotic vertebra, is avoided.

Thus, the improvements based on the use of "shorter screw+plug" include the advantages of the other systems, while also providing the improvement derived from the fact of applying the forces exclusively on the most solid part of the vertebra, i.e. the pedicle. It also avoids the risk of the pull-out strength being lost in osteoporotic vertebrae, since the inner portion of the plug is wider than the outer portion. Finally, with the improvements of the invention, it is not possible to exceed the anterior cortical layer of the vertebra with the screw tip, thereby eliminating the concomitant risks.

Thus, the improvements provide greater security and support when this technique is used in osteoporotic patients in which the density of the bone tissue of the vertebral body is much less.

The improvements of the present invention afford the advantages described above, apart from others which will be readily gathered from the embodiment of the vertebral attachment system with exclusive transpedicular support provided with such improvements, described in further detail hereinafter to facilitate the understanding of the above features, while various details are disclosed at the same time. The present description is accompanied by drawings in which there is shown one embodiment of the invention just as an example and without limitation of the scope thereof.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 shows the screw forming a part of the device for carrying out the system;

FIG. 2 is a side view of a plug forming part of the device;

FIG. 3 is a cross-sectional view of a thread of the plug of the present invention;

FIG. 4 is an end view showing the widened portion of the plug of the present invention;

FIG. 5 is a view of the device, comprising the screw and plug;

FIGS. 6, 7 and 8 show different stages of the system in which the technique for fitting the device is shown;

FIG. 9 corresponds to the prior art, showing the risks involved with the use of a conventionally sized pedicular screw;

FIG. 10 is a plan view from below of a clamp according to an alternative embodiment;

FIG. 11 is a sectional view of the clamp, on the line A–A' of FIG. 10

FIG. 12 is a similar view to that of FIG. 1, in which the clamp includes the screw to be inserted in the pedicular plug; and FIG. 13 is a schematic view of the clamp with the fixing bar and the cylindrical member with the screw and pedicular plug.

DESCRIPTION OF AN EMBODIMENT OF THE INVENTION

With reference. to FIGS. 1 to 9, a device designed for vertebral attachment exclusively with transpedicular support is shown. This device comprises a screw of steel, titanium or any other alloy, designated in general by 1, and a plug 2, of silastic or any other polymer of similar mechanical properties and biocompatibility, or any metal or alloy.

The screw 1 has a threaded portion 3, limited by a radial shoulder 4.

The plug 2 has a radial widening 5 to prevent it from being inserted too far. The shank of said plug is provided with a thread 6. The widened portion 5 is hexagonal in shape to allow it to engage a hollow screwdriver, allowing it to be manipulated.

The plug 2 is of the type having longitudinally extending slits 7 to promote the expansion thereof. Four slits are provides as shown in FIG. 3.

The system comprises a first step in which the pedicle 8 is drilled, with a twist drill 9, of 0.4 cm, as shown in FIG. 6.

In a second step, as shown in FIG. 7, the silastic plug 2 is inserted in the pedicle 8 by screwing into the bore formed with the twist drill.

Finally, in a third step, the threaded portion 3 of the screw 1 is inserted in the plug 2 and screwed into the bore of the plug.

In FIG. 8 the advantages provided by the improvements of the invention over the prior art, shown in FIG. 9, in which the tip 10 of the conventional pedicular screw 11 is shown to be in a position to extend beyond the anterior cortical layer of the vertebra 12 and perforate viscera or blood vessels (intestine 13, aorta 14, vena cava 15.), are clearly to be seen.

With reference to FIGS. 10 to 13, an alternative embodiment is shown of clamp connection means applicable in the vertebral fusion systems by way of pedicular plug and screw and connecting rod.

Such connecting means or clamps are constituted by two parts, designated 16 and 17, respectively.

Part 17 is a cylindrical circular clamp member open at one of the sides thereof and housing therein a ball joint 18, also open at one side thereof.

Part 17 constitutes two hollow cylinders, each attached to one of the open ends of the circular member 16.

The attachment rod 19 is inserted through the circular member 16 and the ball joint 18, For the ball joint to grip the rod firmly, the internal of the ball joint 18 for engaging the rod 19 is provided with a diamond point finish 20.

A screw 21 is inserted through the two portions of the cylindrical member 17 and is then inserted in the pedicular plug 22. Once the screw has been inserted, the system is blocked with a nut, 23.

In FIGS. 10 and 11 the dotted arrow shows the passage of the rod and the solid arrow the passage of the pedicular screw.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

I claim:

1. A method for transpedicular vertebral attachment comprising the steps of:

drilling a pedicle with a twist drill in order to form a hole in the pedicle;

removing the twist drill from the hole thus formed in the pedicle;

screwing a plug into the hole in the pedicle formed by the twist drill, the plug having a first end and a second end and having an opening at the first end thereof which is not inserted into said hole and having a tubular stem being provided with equidistantly spaced radial slits extending lengthwise along the stem at the second end;

inserting a threaded portion of a screw into the opening of the plug; and expanding the plug radially by inserting the threaded portion of the screw whereby anchorage of the plug is established in the pedicle.

2. The method according to claim 1, further comprising the step of using a twist drill of 0.4 cm size.

3. The method according to claim 1, further comprising the step of using a screw which is made of steel, titanium or alloy.

4. The method according to claim 1, further comprising the steps of:

providing a radially widened portion on the plug;

providing a radial shoulder on the screw, the threaded portion of the screw extending from an end of the screw to the radial shoulder, the threaded portion of the screw being slightly longer than a length of the pedicle; and stopping inserting the screw into the hole in the plug by engagement of the radial shoulder with the radially widened portion of the plug.

5. The method according to claim 1, further comprising the steps of:

using a polymer or a metal or an alloy for the plug, the plug being biocompatable with the pedicle, the plug having a radially widened portion, said tubular stem of the plug extending from an end thereof to the radially widened portion, the tubular stem having a length of 3.1 cm and a diameter of 0.5 cm and the radially widened portion forming a hexagonal head having a diagonal measurement of 0.8 cm; and engaging the hexagonal head with a tool for manipulation thereof.

6. The method according to claim 5, further comprising the step of enlarging the radial slits to thereby widen the end of the plug which is screwed into the hole in the pedicle during the step of expanding the plug, the tubular stem having a first circumference adjacent the radially widened portion and having a second circumference at the end which is screwed into the hole in the pedicle, the second circumference being greater than the first circumference after the step of enlarging.

7. The method according to claim 1, further comprising the steps of:

using silastic as the plug, the plug being biocompatable with the pedicle, the plug having a radially widened portion and a tubular stem extending from an end thereof to the radially widened portion, the tubular stem having a length of 3.1 cm and a diameter of 0.5 cm and the radially widen portion forming a hexagonal head having a diagonal measurement of 0.8 cm; and engaging the hexagonal head with a tool for manipulation thereof.

8. The method according to claim 7, further comprising the step of enlarging the radial slits to thereby widen the end of the plug which is screwed into the hole in the pedicle during the step of expanding the plug, the tubular stem having a first circumference adjacent the radially widened portion and having a second circumference at the end which is screwed into the hole in the pedicle, the second circumference being greater than the first circumference after the step of enlarging.

9. A system for transpedicular vertebral attachment comprising:

a twist drill for forming a hole in a pedicle;

a plug having a first end and a second end, the first end of the plug having an opening provided therein, the second end of the plug being insertable into the hole in the pedicle formed by the twist drill and having a tubular stem being provided with equidistantly spaced radial slits extending lengthwise along the stem; and means for expanding the second end of the plug to thereby enlarge the second end to form an anchorage of the slug in the pedicle, the means for expanding comprising a screw which is insertable into the opening in the first end of the plug.

10. The system for transpedicular vertebral attachment according to claim 9, wherein the twist drill has a size of 0.4 cm.

11. The system for transpedicular vertebral attachment according to claim 9, wherein the screw is made of steel, titanium or alloy.

12. The system for transpedicular vertebral attachment according to claim 9, wherein the plug has a radially widened portion and the screw has a radial shoulder, the screw having a threaded portion which extends from an end of the screw to the radial shoulder, the threaded portion of the screw being slightly longer than a length of the pedicle, the radial shoulder of the screw being adapted to engage the radially widened portion of the plug to be able to stop insertion of the screw into the opening in the plug.

13. The system for transpedicular vertebral attachment according to claim 9, wherein the plug is made of one material selected from a polymer, a metal or an alloy and is biocompatable with the pedicle, the plug having a radially widened portion, the tubular stem extending from the second end thereof to the radially widened portion, the tubular stem having a length of 3.1 cm and a diameter of 0.5 cm, and the radially widened portion forming a hexagonal head having a diagonal measurement of 0.8 cm.

14. The system for transpedicular vertebral attachment according to claim 13, wherein the radial slits are enlarged by the means for expanding to thereby widen the second end of the plug, the tubular stem having a first circumference adjacent the radially widened portion and having a second circumference at the end which is screwed into the hole in the pedicle, the second circumference being greater than the first circumference after the means for expanding enlarges the second end of the plug to form an anchorage in the pedicle.

15. The system for transpedicular vertebral attachment according to claim 9, wherein the plug has a radially widened portion and the tubular stem extending from the second end thereof to the radially widened portion, the means for expanding enlarges the radial slits to thereby widen the second end of the plug, the tubular stem having a first circumference adjacent the radially widened portion and having a second circumference at the end which is screwed into the hole in the pedicle, the second circumference being greater than the first circumference after the means for expanding enlarges the second end of the plug to form an anchorage in the pedicle.

16. The system for transpedicular vertebral attachment according to claim 9, wherein the plug is made of silastic and is biocompatible with the pedicle, the plug having a radially widened portion, the tubular stem extending from the second end thereof to the radially widened portion, the tubular stem having a length of 3.1 cm and a diameter of 0.5 cm, and the radially widened portion forming a hexagonal head having a diagonal measurement of 0.8 cm.

17. The system for transpedicular vertebral attachment according to claim 16, wherein the radial slits are enlarged by the means for expanding to thereby widen the second end of the plug, the tubular stem having a first circumference adjacent the radially widened portion and having a second circumference at the end which is screwed into the hole in the pedicle, the second circumference being greater than the first circumference after the means for expanding enlarges the second end of the plug to form an anchorage in the pedicle.

18. A device for connecting an attachment rod and a pedicular plug in a transpedicular vertebral attachment system comprising:

a generally cylindrical, c-shaped member having two ends which form an opening therebetween, the c-shaped member further having a centrally disposed opening, a ball joint being housed in the centrally disposed opening of the c-shaped member, the attachment rod being housed in the ball joint, the ball joint being in direct engagement with the attachment rod;

a pair of hollow cylinders, one of the cylinders being attached to each end of the c-shaped members, a screw being received in both of the hollow cylinders, the screw being insertable in the pedicular plug; and a nut for locking the screw in position in the pair of hollow cylinders.

19. The device for connecting according to claim 18, wherein the ball joint has a diamond point finish in direct contact with the attachment rod.

* * * * *